United States Patent [19]

Richmond et al.

[11] 4,071,029
[45] Jan. 31, 1978

[54] ANGLE HANDPIECE

[75] Inventors: James W. Richmond, Comstock Township, Kalamazoo County; Earl H. Rhodes, Jr., Oshtemo Township, Kalamazoo County, both of Mich.

[73] Assignee: Stryker Corporation, Kalamazoo, Mich.

[21] Appl. No.: 688,567

[22] Filed: May 21, 1976

[51] Int. Cl.$^2$ .................. A61B 17/16; A61B 17/32
[52] U.S. Cl. ............................ 128/305; 128/310; 32/26
[58] Field of Search .............. 128/305, 310; 32/26, 32/27, 48, DIG. 1, DIG. 8

[56] References Cited

U.S. PATENT DOCUMENTS

| 213,662 | 3/1879 | Johnston et al. | 32/26 R |
|---|---|---|---|
| 493,846 | 3/1893 | Weber et al. | 32/27 R |
| 950,759 | 1/1910 | Weiner | 32/26 R |
| 2,851,777 | 9/1958 | Hoffmeister | 32/26 |
| 3,423,068 | 1/1969 | Hall | 253/2 |
| 3,509,629 | 5/1970 | Kidokoro et al. | 32/27 R |
| 3,657,818 | 4/1972 | Garnier | 32/27 R |
| 3,734,652 | 5/1973 | Barnett | 418/70 |
| 3,847,154 | 11/1974 | Nordin | 128/305 |
| 3,909,946 | 10/1975 | Watanabe | 32/26 R |

Primary Examiner—John D. Yasko
Assistant Examiner—Henry J. Recla
Attorney, Agent, or Firm—Blanchard, Flynn, Thiel, Boutell & Tanis

[57] ABSTRACT

A surgical instrument formed by a handpiece assembly and a removable tool assembly. The handpiece assembly includes a housing having integrally interconnected grip and nose portions which are of tubular construction and are positionally related so that the longitudinal direction of the nose portion extends at an angle of 40° with respect to the longitudinal direction of the grip portion. The grip portion contains first and second removable cartridge units, with one cartridge unit containing a motor and the other cartridge unit containing a speed reducer. The tool assembly includes an elongated rotatable tool which is axially confined by and rotatably supported on an elongated support sleeve. The rearward end of the support sleeve is connectible to the front end of the nose portion by a bayonet-type coupling, which also permits the rearward end of the tool to be nonrotatably coupled to a drive shaft rotatably supported in the nose portion.

6 Claims, 3 Drawing Figures

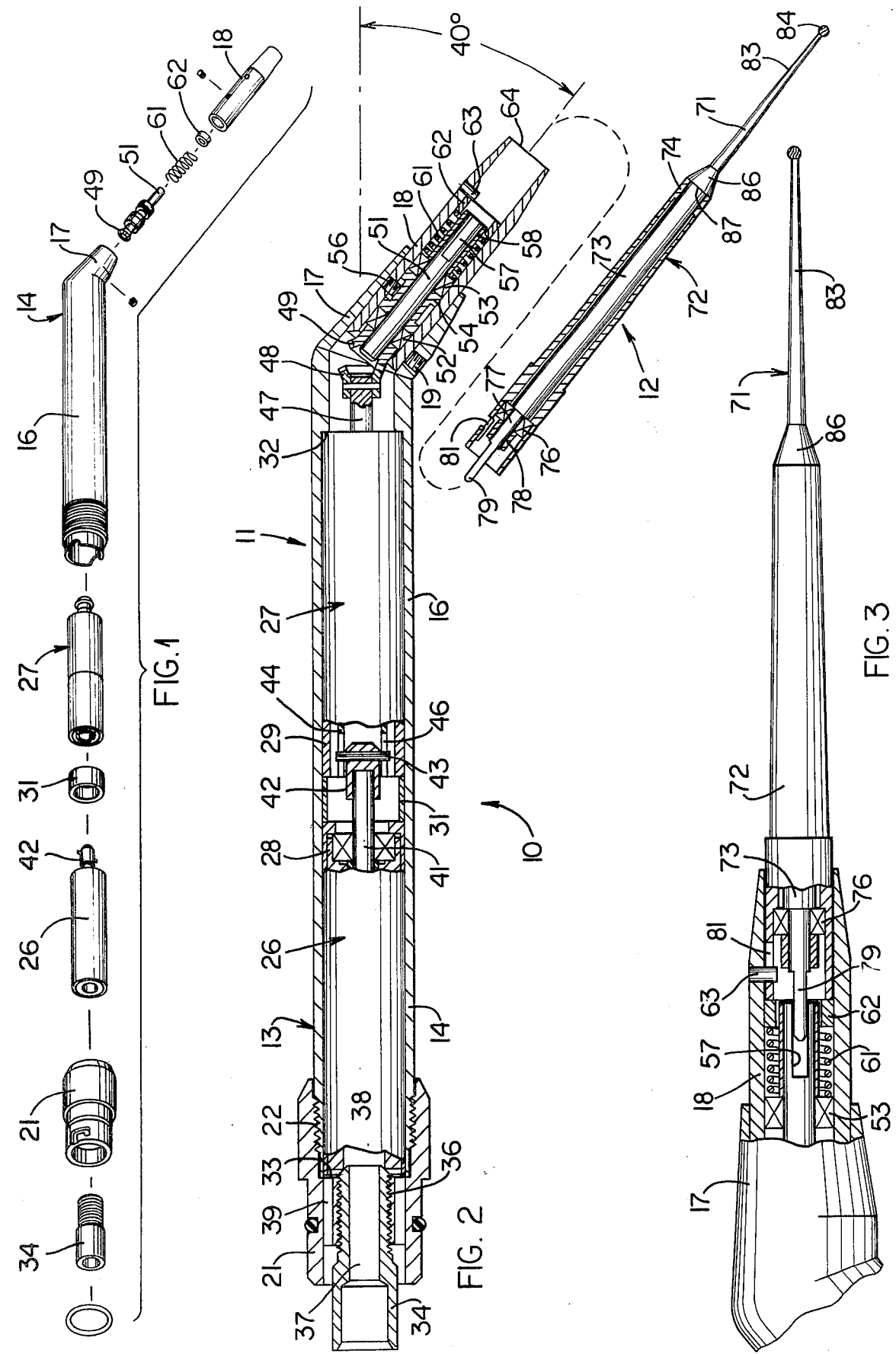

ANGLE HANDPIECE

FIELD OF THE INVENTION

This invention relates to a surgical instrument and, in particular, to an instrument having an improved angled handpiece assembly.

BACKGROUND OF THE INVENTION

In performing surgery, particularly on the ear, it has been conventional to utilize a surgical instrument having an elongated handpiece with a rotatable tool projecting outwardly from the forward end thereof. This instrument is less than satisfactory since the straight handpiece results in the surgeon's hand, where it grips the handpiece, obstructing the surgeon's view of the tool and of the surgical area.

To improve upon such surgical instrument, particularly for use in ear surgery, it has been proposed to utilize an instrument wherein the handpiece assembly is angled. While the handpiece member again includes an elongated gripping portion, it also includes a nose portion for rotatably supporting the tool, which nose portion extends at an angle of 20° relative to the gripping portion. This instrument, however, has been discovered to possess features which make usage of same less than desirable when performing ear surgery. For example, the angular relationship between the nose and hand portions still results in the hand of the surgeon being at least partially disposed within the surgeon's line of sight. This angular relationship also does not provide the surgeon with the desired feel and control which is desired to permit proper manipulation of the instrument during the surgical procedure.

The known surgical instruments of this general type have also possessed other features which have made their use less than satisfactory. For example, these known instruments have normally employed a built-in motor and speed reducer mechanism whereby replacement of the motor and/or speed reducer so as to provide various speed ratios has thus been difficult and time-consuming, since such variations generally require a complete disassembly and rebuilding of the instrument. In addition, these known instruments have often been provided with a tool mounting structure which is less than satisfactory, particularly when the instrument is utilized with an elongated tool such as commonly employed in ear surgery.

The present invention thus relates to an improved surgical instrument which possesses features which makes same highly desirable for use in ear surgery, which instrument overcomes the above-mentioned shortcomings.

More specifically, it is an object of the present invention to provide an improved surgical instrument, as aforesaid, wherein the handpiece has an elongated grip portion and a shorter nose portion, which nose portion extends at an angle of 40° with respect to the longitudinal axis of the grip portion so as to permit optimum gripping, handling and control of the instrument, while maximizing the surgeon's vision of the surgical area and tool.

It is also an object of this invention to provide an improved instrument, as aforesaid, which possesses both a cartridge-type motor and a cartridge-type speed reducer positioned within the handpiece, which cartridges can be easily and quickly removed and interchanged to permit replacement of same for purposes of repair or for producing a different speed ratio.

A further object of this invention is to provide an improved instrument, as aforesaid, which has a tool mounting structure associated with the nose portion of the handpiece for permitting an elongated rotatable tool, such as a burr, to be easily and readily attached to or removed from the instrument, while at the same time providing for proper support of the elongated tool so as to maintain same properly aligned during rotation of the tool.

In addition, this improved structure permits the utilization of an elongated burr having a tapered hub which coacts with a sleevelike mounting member to create a smooth exterior surface which minimizes contamination of the tool, which sleevelike member can be easily connected to or removed from the handpiece assembly.

To summarize the present invention, the surgical instrument is provided with an angled tubular handpiece which includes an elongated grip portion having a cartridge-type motor and a cartridge-type speed reducer removably positioned therein. The rearward end of the grip portion is connected to a suitable source for driving the motor, such as a flexible conduit for supplying pressurized air to the motor. The handpiece has a nose portion fixed to the other end of the grip portion, which nose portion extends at an angle of 40° with respect to the longitudinal direction of the grip portion. This nose portion has a releasable torque-transmitting drive connection associated therewith. A tool assembly is adapted for connection to the nose portion of the handpiece assembly. The tool assembly includes an elongated burr or other suitable tool having an elongated shank rotatably supported within an elongated support sleeve, which support sleeve in turn has coupling structure adapted for releasable connection with further coupling structure mounted within the nose portion.

Other objects, purposes and advantages of the surgical instrument according to this invention will be apparent to persons familiar with instruments of this type upon reading the following specification and inspecting the accompanying drawings.

BRIEF DESCRIPTION OF THE DRAWINGS

FIG. 1 is an exploded, perspective view of the handpiece assembly.

FIG. 2 is an enlarged, cross-sectional view of the instrument, parts thereof being broken away, and showing the tool assembly separated from the handpiece assembly.

FIG. 3 is a fragmentary view, partially in cross-section, showing the tool assembly coupled to the nose portion of the handpiece assembly.

Certain terminology will be used in the following description for convenience in reference only and will not be limiting. For example, the words "rightwardly," "leftwardly," "upwardly" and "downwardly" will refer to directions in the drawings to which reference is made. The word "forward" will refer to the tool end of the instrument, namely the rightward end as appearing in FIGS. 1-3, whereas the word "rearward" will refer to the leftward end of the instrument as appearing in FIGS. 1-3. The words "inwardly" and "outwardly" will refer to directions toward and away from, respectively, the geometric center of the instrument and designated parts thereof. Said terminology will include the words specifically mentioned, derivatives thereof and words of similar import.

DETAILED DESCRIPTION

FIG. 2 illustrates therein a hand-held surgical instrument 10 which includes an angled handpiece assembly 11 to which is attached a tool assembly 12.

The handpiece assembly 11 includes an angled handpiece 13 which is formed primarily by a housing member 14 having a straight tubular grip portion 16 of substantial length and a short tubular nose part 17 integrally connected to the forward end of the grip portion. The longitudinal axis of the nose part 17 is inclined at an angle of 40° relative to the longitudinal axis of the grip portion 16, which angle is measured as illustrated in FIG. 2. Handpiece 13 also includes a tubular member 18 which is fixedly positioned within the nose part 17 as by a set screw 19, and projects outwardly therefrom. The part 17 and tubular member 18 thus form the nose portion of the handpiece. An adapter sleeve 21 also forms part of the housing 13 and is fixedly connected to the rearward end of the housing member 14 by means of a threaded connection 22 therebetween.

A cartridge-type motor 26 is removably positioned within the grip portion 16, which motor is connected in series with a cartridge-type speed reducer 27, which is also removably positioned within the grip portion 16. These cartridges 26 and 27 have outer sleevelike housings 28 and 29, respectively, so that the individual cartridges can each be slidably inserted into and removed from the rearward end of the grip portion 16. Both the motor and speed reducer cartridges are entirely self-contained so that each can be handled as a single unit. The motor cartridge 26 contains therein a suitable motor, preferably a conventional pneumatic motor, so as to permit the desired high-sped rotation of the surgical tool. The specific configuration of the speed reducer disposed within the cartridge 27 can also be of conventional configuration, such as a gear-type speed reducer, so as to achieve the desired speed ratio between the input and output ends thereof.

The forward end of the speed reducer cartridge 27 is adapted to abut against a shoulder 32 formed internally of the grip portion 16 for defining the innermost position of the cartridge. A spacer sleeve 31 is slidably received within the grip portion 16 and disposed between the housings of the cartridges 26 and 27 for maintaining same in the desired axially-spaced relationship. The rearward end of the motor cartridge in turn abuts against an internal annular shoulder 33 formed on the adapter sleeve 21, whereby the cartridges 26 and 27 are stationarily confined within a housing 13.

To supply pressure fluid, namely air, to the motor cartridge 26, there is provided an intake tube 34 fixedly disposed concentrically within the adapter sleeve 21 as by means of a threaded connection 36 therebetween. The inner end of intake tube 34 is disposed in bearing engagement with the adjacent rearward end of the motor cartridge 26 so that the air supply passage 37 through the tube 34 is thus in continuous communication with the inlet passage 38 formed in the motor cartridge 26. To permit discharge of air from the motor, there is provided a plurality of small discharge passages 39 formed in the adapter sleeve 21 and opening axially through the rearward end thereof so that the air is thus discharged through a passageway which surrounds the intake tube 34. The adapter sleeve 21 and intake tube 34 are conventionally connected to an elongated flexible conduit assembly (not shown) having concentric inner and outer flexible tubes so that the pressurized supply air can be supplied through the inner tube and the discharge air removed through the outer tube.

The cartridge motor unit 26 has an output shaft 41 projecting therefrom and provided with a cylindrical guide portion 42 thereon, which guide portion is adapted to be slidably received within the rearward end of the input shaft 44 associated with the speed reducer unit 27. This guide portion 42 has a drive pin 43 projecting radially therethrough, the exposed ends of which are adapted to be slidably inserted into a pair of diametrically opposed, axially extending slots 46 formed in the rearward end of the shaft 44.

The speed reducer unit 27 has an output shaft 47 which is coaxially aligned with the input shaft 44 and projects outwardly from the opposite end of the cartridge housing. This output shaft 47 has a gear 48 secured thereto and disposed in meshing engagement with a further gear 49 secured to a drive shaft 51 which is coaxially rotatably supported in the tubular member 18. The gears 48 and 49, in the illustrated embodiment, comprise bevel gears so as to accommodate the 40° change in direction between the axes of the shafts 47 and 51. However, other types of driving connections can also be provided for drivingly interconnecting these shafts.

The drive shaft 51 is rotatably supported within member 18 by conventional anti-friction bearings 52 and 53, which bearings are spaced apart by an intermediate annular spacer 54 which is secured in position by a set screw 56. The forward end of shaft 51 extends beyond the frontmost bearing 53 but is spaced inwardly a substantial distance from the free end 64 of the tubular member 18. This forward end of shaft 51 has a slot 57 extending diametrically thereacross, which slot extends inwardly through a preselected distance from the front end of the shaft.

The projecting forward end of shaft 51 is surrounded by a thin sleeve 58, which in turn is surrounded by a conventional coiled compression spring 61, the rearward end of which bears against the bearing 53. The other end of spring 61 bears against a ring member 62 which is slidably disposed within the tubular member 18, whereby this ring is normally urged into engagement with a pin 63 which is fixed to the tubular member 18 and projects radially inwardly through a short distance. This pin 63 is spaced inwardly from the open end 64 of the tubular member 18, but is displaced forwardly from the free end of the drive shaft 51.

Considering now the tool assembly 12, same includes an elongated rotatable tool 71 which is partially surrounded by and rotatably supported within an elongated support sleeve 72. Tool 71 has an elongated cylindrical shank 73 which extends throughout a major portion of the axial length of the sleeve 72, which sleeve has a sleevelike bearing portion 74 at the forward end thereof for rotatably supporting the forward end of the shank 73. A further bearing 76, in this case a conventional anti-friction bearing, is provided adjacent the rearward end of the support sleeve 72 and is disposed in engagement with a stub shaft portion 77 which projects coaxially from the rearward end of the shank 73. A locking sleeve 78 is secured to the stub shaft portion 77 and is disposed on the opposite side of the bearing 76 so as to axially secure the cylindrical shank 73 within the support sleeve 72.

The tool 71 also has a substantially flat tongue 79 projecting axially from the rearward end thereof, which tongue projects axially beyond the support sleeve 72 and is adapted to be slidably received within the slot 57 formed in the drive shaft 51. This rearward end of support sleeve 72 also has an L-shaped slot 81 formed through the sidewall thereof, which slot has one leg portion thereof extending axially inwardly from the free end of the sleeve and connected to a further portion which extends circumferentially of the sleeve. This slot 81 coacts with the fixed pin 63 secured to the support member 18 for creating a bayonet-type coupling whereby the tool assembly 12 can be secured to the nose portion of the handpiece assembly as illustrated in FIG. 3.

The forward end of the tool assembly 71 is formed by an elongated quill-like shaft 83 which projects axially a substantial distance beyond the forward end of the support sleeve 72. This quill-like shaft is, in the illustrated embodiment, of a tapered configuration and is provided with a conventional cutting member 84, such as a ball-like burr, at the free end thereof. Tool 71 also has a conical portion 86 joined bewteen the shank portion 73 and the quill shaft 83, which conical portion 86 terminates in a rear shoulder 87 which abuts against the free end of the sleeve member 72. This conical portion 86 has the outer surface thereof diverging smoothly in a radially outer direction so that the maximum diameter of the conical portion, as located adjacent the shoulder 87, is substantially equal to the external diameter of the adjacent end of the sleeve member 72.

OPERATION

The operation of the surgical instrument 10 will be briefly described to ensure a complete understanding thereof.

When it is desired to mount the tool assembly 12 on the handpiece assembly 11, the rearward end of the support sleeve 72 is slidably inserted into the open end 64 of the tubular member 18 so that the pin 63 is aligned with the open end of the L-shaped slot 81. The tool assembly 12 is pushed inwardly a sufficient extend so that the tongue 79 of the tool 71 projects into the slot 57 formed in the end of the drive shaft 51, thereby nonrotatably connecting the tool 71 to the drive shaft 51. This axial insertion of the tool assembly into the support member 18 is sufficient so that the pin 63 moves into and bottoms against the end of the L-shaped slot 81, whereupon the sleeve 72 is then relatively rotated so that pin 63 becomes locked within the slot 81 to thereby securely axially couple the sleeve 72 to the tubular member 18. The pin 63 and slot 81 thus form a bayonet-type coupling which can be disconnected by reversing the manipulations explained above so as to permit removal of the tool assembly. During insertion of the rearward end of the sleeve 72 into the tubular member 18, the support sleeve 72 engages the ring 62 and axially displaces same inwardly in opposition to the urging of the spring 61, whereby this spring in turn continuously exerts an outward resilient force against the sleeve 72 after same has been lockingly connected to the tubular member 18 by the pin 61 so as to prevent accidental disconnection of the bayonet-type coupling formed by the pin 63 and slot 81.

When assembled as described above, the instrument 10 can then be utilized by supplying pressurized air through a suitable conduit (not shown) into the intake tube 34 and through the passage 37 and 38 to the motor provided within the cartridge unit 26. This results in a high-speed rotation of the output shaft 41, which is then transmitted through the speed reducer cartridge unit 27 so as to drive the output shaft 47 thereof. This in turn drives the drive shaft 51 through the gears 47 and 48, and drive shaft 51 causes a corresponding high-speed rotation of the tool 71.

When the instrument 10 is being utilized, the surgeon will grip the elongated grip portion 16. However, since the nose portion 17 and the tool 71 extend at an angle of 40° with respect to the longitudinal axis of the grip portion 16, this angle enables the surgeon to see longitudinally along the nose portion and along the tool without having his hand positioned so as to interfere with his vision, whereby the surgeon thus has unrestricted unobstructed visability with respect to the tool and the surgical area. In addition, the 40° angle between the grip and nose portions permits the surgeon to have a gripping engagement with the handpiece assembly which is comfortable and which also permits the surgeon to have desirable control over the manipulation and movement of the handpiece so as to permit precise movement of the burr 84.

Due to the manner in which the conical portion 86 on the tool 71 abuts the end of the sleeve 72, this conical portion not only provides a smooth profile which assists in maximizing the surgeon's vision but it also creates a relatively smooth outer surface and closes the outer end of the sleeve 72 so as to effectively prevent undesired materials from entering into the interior of the support sleeve.

Should it be necessary to replace or repair the pneumatic drive motor, the complete cartridge unit 26 can be easily slidably removed from the housing by removing the adapter sleeve 21 so that the cartridge 26 can then be slidably removed from the grip portion 16. Similarly, if a desired speed ratio is desired, same can also be achieved by removing the speed reducer cartridge 27 by slidably moving same out through the rear end of the grip portion and replacing same by a new cartridge-type speed reducer unit having the desired speed ratio. It will also be appreciated that the motor within the cartridge unit 26 need not be of pneumatic type, but could be electrically operated if desired.

While it is recognized that surgical instruments for performing ear surgery have been developed which employ a handpiece assembly having the nose portion extending at a 20° angle, as briefly described, these known instruments have proven somewhat undesirable in view of the extremely restricted visability of the surgical area. In addition, while surgical instruments employing angled handpieces have also been developed wherein the nose portion of the handpiece extends at an angle of 45°, nevertheless even these assemblies are not believed satisfactory for the purposes of the present invention since they have not been developed for use with ear surgery. Further, applicant has determined that the 40° angle of the present invention is more desirable than a 45° angle since it results in optimum visability while at the same time providing optimum comfort to the surgeon with respect to his ability to manually manipulate and control the instrument.

Although a particular preferred embodiment of the invention has been disclosed above for illustrative purposes, it will be understood that variations or modifications thereof which lie within the scope of the appended claims are fully contemplated.

The embodiments of the invention in which an exclusive property or privilege is claimed are defined as follows:

1. In a surgical instrument, particularly for ear surgery, having a handpiece assembly formed by an angled housing having a motor mounted therein, rotatable connecting means disposed within said housing for driving connection with a tool assembly, and drive transmitting means interconnected between said motor and said connecting means, comprising the improvement wherein:

said angled housing includes an elongated tubular grip portion having said motor positioned therein and an elongated tubular nose portion fixedly connected to one end of said grip portion, said grip portion having a length which is several times longer than the length of said nose portion;

said nose portion having said connecting means positioned therein, and said nose portion extending in a direction which is inclined at an angle of 40° relative to the longitudinal direction of said grip portion; and said tool assembly comprising a tool unit removably attached to said nose portion and drivably connected to said connecting means;

said tool unit including an elongated support sleeve removably inserted into the open free end of said nose portion, said nose portion and the rear end of said support sleeve having cooperating means forming a disconnectible connection for fixedly but releasably connecting said support sleeve to said nose portion so that said support sleeve is coaxially aligned with and forms an outwardly projecting extension from said nose portion;

said tool unit further including an elongated tool axially fixedly connected to said support sleeve, said tool having an elongated cylindrical shank disposed within and coaxially rotatably supported by said support sleeve, said shank having a driving portion on the rearward end thereof adapted for driving connection with said rotatable connecting means, and said tool including a part thereof projecting coaxially outwardly beyond the front end of said support sleeve.

2. An instrument according to claim 1, wherein said part comprises an elongated quill-like shaft having a cutting element on the free end thereof, said quill-like shaft being joined to said cylindrical shank by an intermediate enlargement which has a conical exterior configuration which slopes outwardly from the quill shaft so as to terminate in an abutment surface which is disposed directly adjacent the free end of said support sleeve, the maximum diameter of said enlargement as disposed adjacent said abutment surface being substantially equal to the exterior diameter of the adjacent end of said support sleeve.

3. An instrument according to claim 2, wherein said drive transmitting means includes speed reducer means disposed within a first cartridge unit which is removably positioned within said grip portion, said motor being mounted within a second cartridge unit which is removably positioned within said grip portion, said first and second cartridge units being disposed in series within said grip portion and being removable through the outer end of said grip portion, and said housing having removable means associated with the other end of said grip portion for normally maintaining said first and second cartridge units fixedly positioned within said grip portion.

4. An instrument according to claim 1, wherein said cooperating means includes an L-shaped slot formed in the rearward end of said support sleeve and a projection fixed to said nose portion, said projection being spaced inwardly from the free end of said nose portion and projecting into the interior thereof so as to be receivable within said L-shaped slot to form a bayonet-type connection whereby said support sleeve can be fixedly but releasably attached to said nose portion, said nose portion having a ring member slidably supported therein, said ring member being positioned inwardly from said projection, and spring means normally urging said ring member toward and into engagement with said projection, whereby said ring member is urged into engagement with the rearward end of said support sleeve when same is connected to said nose portion.

5. An instrument according to claim 6, wherein said rotatable connecting means includes a drive shaft rotatably supported within said nose portion and having the forward end thereof spaced inwardly from the free end of said nose portion, said drive shaft having a slot extending diametrically thereacross, and the driving portion on said tool comprising a flat platelike tongue projecting axially from the rearward end of said cylindrical shank, said tongue being axially slidably insertible into said slot for creating a nonrotatable connection between said drive shaft and said tool.

6. In a hand piece assembly for a surgical instrument, the improvement comprising:

angled housing means including an elongated tubular grip portion having one end thereof fixedly connected to an elongated tubular nose portion, the longitudinal direction of said nose portion extending at an angle relative to the longitudinal direction of said grip portion;

a first removable cartridge unit positioned within said grip portion, said first cartridge unit having motor means disposed therein;

a second removable cartridge unit disposed within said grip portion and positioned axially in series with said first cartridge unit, said second cartridge unit having speed reducer means disposed therein;

first disconnectible coupling means for permitting the transmission of driving torque from said motor means to said speed reducer means;

removable means fixedly associated with the other end of said tubular portion for holding said cartridges within said grip portion;

a rotatable drive shaft coaxial with and rotatably supported within said tubular nose portion, and gear means disposed substantially at the intersection between said grip and nose portions for drivingly connecting said drive shaft to the output of said speed reducer means;

means associated with said nose portion adjacent the free end thereof for permitting a rotatable tool to be drivingly connected to said drive shaft, said last-mentioned means including a narrow slot formed within and extending diametrically of said drive shaft and opening outwardly through the free end thereof; and a unitized tool assembly for releasable attachment to said nose portion, said tool assembly including an elongated support sleeve having a rearward end thereof insertible into the free end of said nose portion, and first and second cooperating coupling means respectively formed on said nose portion and the rearward end of said support sleeve for fixedly but releasably connecting said support sleeve to said nose portion; said tool assembly also including an elongated tool coaxially aligned with and rotatably supported within said support sleeve, said tool being axially fixedly mounted on said support sleeve and having a driving portion in the form of a flat tongue projecting axially from the rearward end thereof, said tongue being slidably insertible into the slot formed in said drive shaft for nonrotatably coupling said tool to said drive shaft, said tool having a shaft portion projecting outwardly from the forward end of said support sleeve and terminating in a cutting element, said support shaft adjacent the forward end of said support sleeve having a conical enlargement which enlarges smoothly to an outer diameter which is substantially equal to the outer diameter of the adjacent end of said support sleeve, said conical enlargement terminating in a shoulder which is disposed adjacent and substantially abuts the forward end of said support sleeve.

* * * * *

UNITED STATES PATENT AND TRADEMARK OFFICE
CERTIFICATE OF CORRECTION

PATENT NO. : 4 071 029
DATED : January 31, 1978
INVENTOR(S) : James W. Richmond and Earl H. Rhodes, Jr.

It is certified that error appears in the above-identified patent and that said Letters Patent are hereby corrected as shown below:

Column 8, line 33; change "claim 6" to ---claim 4---.

Signed and Sealed this

Thirteenth Day of June 1978

[SEAL]

Attest:

RUTH C. MASON
*Attesting Officer*

DONALD W. BANNER
*Commissioner of Patents and Trademarks*